United States Patent [19]

Hartle et al.

[11] 4,266,947
[45] May 12, 1981

[54] GASOLINE COMPOSITION CONTAINING ARYL O-AMINOAZIDES

[75] Inventors: Robert J. Hartle, Gibsonia; Gary M. Singerman, Monroeville, both of Pa.

[73] Assignee: Gulf Research & Development Company, Pittsburgh, Pa.

[21] Appl. No.: 151,812

[22] Filed: May 21, 1980

[51] Int. Cl.³ ............................................... C10L 1/22
[52] U.S. Cl. ........................................... 44/68; 44/69; 44/74; 252/386
[58] Field of Search ................ 44/68, 69, 74; 252/386

[56] References Cited

U.S. PATENT DOCUMENTS

| | | | |
|---|---|---|---|
| 2,413,262 | 12/1946 | Stirton | 44/74 |
| 2,819,953 | 1/1958 | Brown et al. | 44/74 |
| 3,212,867 | 10/1965 | Ockerbloom | 44/69 |
| 3,224,972 | 12/1965 | Orloff et al. | 44/74 |

*Primary Examiner*—Winston A. Douglas
*Assistant Examiner*—J. V. Howard

[57] ABSTRACT

Gasoline motor fuel compositions which contain minor amounts of an aryl o-aminoazide, such as o-azidoaniline, to impart improved antiknock characteristics and greater oxidation stability to the gasoline.

11 Claims, No Drawings

GASOLINE COMPOSITION CONTAINING ARYL O-AMINOAZIDES

This is a continuation-in-part of our patent application Ser. No. 83,297, filed Oct. 10, 1979, now abandoned.

SUMMARY OF THE INVENTION

This invention relates to gasoline motor fuel compositions of improved antiknock characteristics and greater oxidation stability.

DESCRIPTION OF THE INVENTION

We have discovered a class of metal-free antiknock agents which are capable of substantial improvement in the antiknock properties of a motor gasoline and which also provide a surprising improvement in the oxidation stability of the motor fuel.

The antiknock agents and antioxidants of our invention are aryl o-aminoazides. Surprisingly, we have discovered that the meta- and para-aminoazides as well as the N-substituted o-aminoazides are proknocks, that is, they increase the knocking characteristics of motor gasoline. The o-aminoazides have the following general formula

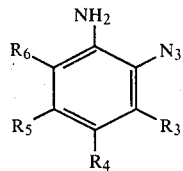

wherein each R group is independently selected from hydrogen, alkyl having from one to about four carbon atoms, alkenyl having from two to about four carbon atoms, haloalkyl having from one to about four carbon atoms, aryl having from six to about ten carbon atoms, cycloalkyl having from five to about eight carbon atoms, alkoxy having from one to about four carbon atoms, carbalkoxy having from two to about five carbon atoms, carbaryloxy having from seven to about nine carbon atoms, alkylamino having from one to about four carbon atoms, acyl having from two to about five carbon atoms, hydroxyl, amino, cyano, nitro, halo and halophenyl, or wherein any two adjacent R groups containing a total of four carbon atoms are joined together in a saturated or unsaturated ring.

Compounds which are useful gasoline additives in accordance with our invention in addition to o-azidoaniline include the following:
2-Azido-3-methylaniline
2-Azido-4-methylaniline
2-Azido-5-methylaniline
2-Azido-6-methylaniline
2-Azido-3,4-dimethylaniline
2-Azido-4,5-dimethylaniline
2-Azido-5,6-dimethylaniline
2-Azido-3,5-dimethylaniline
2-Azido-3,4,5-trimethylaniline
2-Azido-3,4,6-trimethylaniline
2-Azido-3,5,6-trimethylaniline
2-Azido-4,5,6-trimethylaniline
2-Azido-3,4,5,6-tetramethylaniline
2-Azido-3-ethylaniline
2-Azido-4-isopropylaniline
2-Azido-4-tert.butylaniline
2-Azido-5-propylaniline
2-Azido-5-tert.butylaniline
2-Amino-3-azidostyrene
3-Amino-4-azidostyrene
3-Amino-4-azidoisopropenylbenzene
2-Azido-4-methoxyaniline
2-Azido-5-methoxyaniline
2-Azido-6-methoxyaniline
2-Azido-4,5-dimethoxyaniline
2-Azido-5,6-dimethoxyaniline
2-Azido-3,5-dimethoxyaniline
2-Azido-5-isopropoxyaniline
2-Azido-5-ethoxyaniline
2-Azido-4-n-butoxyaniline
2-Azido-4-isobutoxyaniline
2-Azido-4-fluoroaniline
2-Azido-4-chloroaniline
2-Azido-4-bromoaniline
2-Azido-4-iodoaniline
2-Azido-5-chloroaniline
2-Azido-6-fluoroaniline
2-Azido-3-fluoroaniline
2-Azido-4,5-difluoroaniline
2-Azido-5,6-dichloroaniline
2-Azido-4,5,6-trichloroaniline
2-Azido-3,4,5,6-tetrachloroaniline
2-Azido-4,5-diiodoaniline
2-Azido-3,4-diiodoaniline
2-Azido-4-chloro-5-methylaniline
2-Azido-5-chloro-6-methylaniline
2-Azido-3-fluoro-5-methylaniline
2-Azido-3-fluoro-4-isobutylaniline
2-Azido-4-iodo-5-methylaniline
2-Azido-4-bromo-5-ethylaniline Useful gasoline additives in accordance with our invention additionally include the following:
2-Amino-3-azidobiphenyl
3-Methyl-2'-amino-3'-azidobiphenyl
3-Methyl-3'-amino-4'-azidobiphenyl
3-tert.Butyl-3'-amino-4'-azidobiphenyl
2,2',4-Trimethyl-3'-amino-4'-azidobiphenyl
2,4-Dichloro-2'-amino-3'-azidobiphenyl
4-Fluoro-2'-iodo-3'-amino-4'-azidobiphenyl
2-Azido-4-cyclohexylaniline
2-Azido-5-cyclohexylaniline
2-Azido-5-(2-methylcyclopentyl)aniline
Methyl-3-amino-4-azidobenzoate
Ethyl-4-amino-5-azidobenzoate
Propyl-2-amino-3-azidobenzoate
Phenyl-3-amino-4-azidobenzoate
2-Azido-1-naphthylamine
3-Azido-2-naphthylamine
1-Azido-2-naphthylamine
2-Azido-1,3-diaminonaphthalene
1-Azido-2-aminotetrahydronaphthalene
3-Amino-4-azidophenol
4-Amino-3-azidophenol
3-Amino-4-azidobenzyl alcohol
1-Amino-2-Azido-4-naphthol
1,3-Diamino-2-azidobenzene
1,4-Diamino-2-azidobenzene
1,5-Diamino-2-azidobenzene
1,6-Diamino-2-azidobenzene
1-Amino-4-(N,N-dimethylamino)2-azidobenzene
2-Amino-3-azido-acetophenone
3-Amino-4-azido-acetophenone
4-Amino-5-azido-acetophenone 4-Amino-5-azido-n-butyrophenone
2-Azido-4-nitroaniline
2-Azido-4-trifluoromethylaniline
2-Azido-5-trifluoromethylaniline
2-Azido-4,6-bis(trifluoromethyl)aniline
2-Azido-4-cyanoaniline
2-Azido-5-cyanoaniline The gasoline fuel composition desirably contains from about 0.1 to about 50 grams of the aryl o-aminoazide antiknock and oxidation stabilizing agent per gallon and preferably from about 0.5 to about 15 grams per gallon.

The aryl o-aminoazides can be prepared by the method of Smith et al, J. Am. Chem. Soc. 84, 485 (1962). Thus, in order to product o-azidoaniline, o-nitroaniline is used as the initial reactant. In producing the ring-substituted o-azidoanilines, o-nitroaniline containing the desired ring substituent or substituents is used. In like manner, the polynuclear aryl o-aminoazides are prepared from the corresponding o-nitronaphthyl amines and the o-nitrotetrahydronaphthyl amines. A typical preparation is set out in Example 1.

EXAMPLE 1

Preparation of 2-Azido-4-fluoroaniline.

A 25 gram portion (0.16 mol) of 2-nitro-4-fluoroaniline was mixed with 24 grams of phthalic anhydride and the mixture was heated at 180°–210° C. for two hours with slow stirring. After evolution of water was complete, the mixture was allowed to cool. It was ground to a powder and treated with three 100 cc. portions of boiling ethanol. The residue was crude N(2-nitro-4-fluorophenyl)phthalimide (mp. 238°–240° C.). A 36 gram (0.126 mol.) portion of this product was dissolved in one liter of acetone containing 108 cc. of acetic acid and 108 cc. of water. The solution was refluxed and treated with a total of 84 grams of iron powder added in small portions. After three hours refluxing, the mixture was filtered while hot and the filtrate was neutralized with saturated sodium carbonate solution. The mixture was filtered and the filtrate poured into about three liters of ice water. N(2-Amino-4-fluorophenyl)phthalimide precipitated out. This product melted at 190°–193° C. The amine was diazotized in 1500 cc. of water containing 200 cc. concentrated hydrochloric acid by treating with a solution of 12 grams of sodium nitrite in 50 cc. of water at 0°–5° C. After stirring three hours at 0°–5° C., the solution was filtered and the filtrate was treated dropwise with a solution of 8.2 grams of sodium azide in 50 cc. of water. After about one hour, evolution of nitrogen had stopped. The white solid was removed on a filter, washed with water, and vacuum dried. The product, N(2-azido-4-fluorophenyl)phthalimide decomposed with the evolution of nitrogen at 200°–205° C.

This material was suspended in 325 cc. of 95 percent ethanol and treated with 4.0 grams of 95 percent hydrazine. The mixture was stirred for two hours at room temperature. The addition of 160 cc. of water and 50 cc. of 20 percent sodium hydroxide solution caused the solid to dissolve. This mixture was filtered into about two liters of ice water. The precipitate of 2-azido-4-fluoroaniline was removed on a filter, washed with water and vacuum dried (mp. 44° C.). It decomposes with evolution of nitrogen between 75° and 100° C.

EXAMPLES 2–7

A series of motor fuel compositions were tested for octane ratings by the motor method (MON by ASTM D2700) and the research method (RON by ASTM D2699) using a clear commercial automotive gasoline having a MON of 84.4 and an RON of 92.6. In these experiments various o-azidoanilines were tested using four grams of the additive per gallon of gasoline in each test. The results of these experiments are set out in Table I in which each listed difference in octane numbers is based on consecutive, matched determinations with the o-azidoaniline and the substituted o-azidoanilines present and absent.

TABLE I

| Example | 2-azidoaniline | ΔMON | ΔRON |
|---|---|---|---|
| 2 | unsubstituted | +0.5 | +1.2 |
| 3 | 4-methyl | +0.3 | +0.8 |
| 4 | 6-methyl | 0 | +0.6 |
| 5 | 4,5-dimethyl | +0.4 | +1.4 |
| 6 | 4-methoxy | +0.2 | +1.1 |
| 7 | 4-fluoro | +0.3 | +1.0 |

EXAMPLES 8–10

Example 2 was repeated using different test gasolines. The Primary Reference Fuels (PRF) are combinations of isooctane and heptane. Indolene is a standard test gasoline of Standard Oil Company of Indiana which is in general use in the industry. Four grams of o-azidoaniline were added per gallon of gasoline. The octane numbers of the fuels and the test results are set out in Table II.

TABLE II

| Ex. | Gasoline | MON | RON | ΔMON | ΔRON |
|---|---|---|---|---|---|
| 2 | commercial | 84.4 | 92.6 | +0.5 | +1.2 |
| 8 | 80 PRF | 80.0 | 80.0 | +0.8 | +1.3 |
| 9 | 90 PRF | 89.7 | 89.8 | +0.6 | +1.0 |
| 10 | Indolene | 88.6 | 98.4 | +0.4 | +0.8 |

EXAMPLES 11–13

The octane rating of several commercial gasolines containing a known metallic antiknock compound were compared before and after the addition of four grams of o-azidoaniline per gallon of gasoline. The results are set out in Table III.

TABLE III

| Ex. | Metallic antiknock | Before MON | Before RON | After ΔMON | After ΔRON |
|---|---|---|---|---|---|
| 2 | none | 84.4 | 92.6 | +0.5 | +1.2 |
| 11 | TEL | 86.5 | 93.6 | +0.7 | +0.5 |
| 12 | MMT | 84.6 | 94.8 | +0.4 | +0.7 |
| 13[a] | Ce(tod)$_4$ | 84.9 | 94.6 | +0.1 | +0.7 |

TEL tetraethyl lead, 1.5 g.Pb/gal.
MMT manganese methylcyclopentadienyl tricarbonyl, 0.0625 g. Mn/gal.
Ce(tod)$_4$ tetrakis(2,2,7-trimethyl-3,5-octanedianato)-cerium, 0.3 g. Ce/gal.
[a]also contained 4 g./gal. of 2,2,7-trimethyl-3,5-octanedione.

EXAMPLES 14–23

The experiments of Examples 2–7 were repeated in the same gasoline using different aryl azido compounds which were found to be proknocks. These compounds were added in an amount of four grams per gallon of gasoline. The results of these tests are set out in Table IV.

TABLE IV

| Ex. | Aryl azide | ΔMON | ΔRON |
|---|---|---|---|
| 14 | 3-azidoaniline | −0.7 | +0.1 |
| 15 | 4-azidoaniline | −0.7 | −0.4 |
| 16 | 2-methoxy-5-azidoaniline | −1.1 | −2.0 |
| 17 | o-azidonitrobenzene | −0.4 | −0.2 |
| 18 | o-azidotoluene | −0.6 | −1.5 |
| 19 | 3-azido-4-methoxytoluene | −0.3 | −0.9 |
| 20 | o-azidochlorobenzene | −0.6 | −1.5 |
| 21 | 2-azido-N-methylaniline | −0.6 | −0.8 |
| 22 | 2-azido-N,N-dimethylaniline | −1.1 | −2.6 |
| 23 | 2-azido-N-methylacetanilide | −0.2 | −0.5 |

EXAMPLES 24–28

A series of experiments were carried out to compare o-azidoaniline with other nonmetallic octane improvers on a weight basis, including one antiknock agent and three antiknock blending agents. The comparison is made at that concentration in weight percent for each agent at which the average increase of ΔMON and ΔRON, that is (ΔMON+ΔRON)/2, is one octane number. The results are set out in Table V which also lists the relative activity on a weight basis with N-methylaniline normalized to an activity of 1.0.

TABLE V

| Ex. | Additive | Wt. % | Relative activity |
|---|---|---|---|
| 24 | o-azidoaniline | 0.17 | 3.6 |
| 25 | N-methylaniline | 0.62 | 1.0 |
| 26 | methanol | 2.8 | 0.20 |
| 27 | ethanol | 2.5 | 0.22 |
| 28 | methyl t-butyl ether | 4.2 | 0.14 |

In further exemplification of this invention, the above listed compounds are separately added to motor gasoline in appropriate amount and are found to significantly improve the octane rating of the gasoline.

EXAMPLE 29

The antioxidant properties of the o-azidoanilines were studied in two gasoline base stocks. Pertinent data on these base stocks are set out in Table VI in which gasoline base stock A is a light fluid catalytic cracking fraction and gasoline base stock B is a commercial unleaded gasoline.

TABLE VI

| | A | B |
|---|---|---|
| API gravity | 62.8 | 67.9 |
| Hydrocarbon analysis | | |
| aromatics, % by vol. | 17.0 | 12.5 |
| olefins, % by vol. | 35.0 | 14.5 |
| saturates, % by vol. | 48.0 | 73.0 |
| Knock ratings | | |
| RON, ASTM D2699 | 92.1 | 92.6 |
| MON, ASTM D2700 | 80.5 | 84.4 |
| Distillation | | |
| overpoint, °F. | 103 | 78 |
| 10% | 132 | 110 |
| 50% | 184 | 199 |
| 90% | 285 | 310 |
| endpoint | 356 | 401 |
| Sulfur, ppm. | 184 | 185 |
| Bromine No. | 70 | — |

These two gasoline base stocks were tested for oxidation stability in accordance with ASTM D525. The data is set out in Table VII in which 0.10 weight percent is 2.76 grams per gallon of the o-azidoaniline. The test was not extended beyond 1,440 minutes (24 hours).

TABLE VII

| Antioxidant | Amount, wt. % | Minutes A | B |
|---|---|---|---|
| none | — | 60 | 720 |
| o-azidoaniline | 0.01 | 60 | — |
| o-azidoaniline | 0.05 | 150 | — |
| o-azidoaniline | 0.10 | >1,440 | — |
| o-azidoaniline | 0.15 | — | >1,440 |
| 2-azido-4-methylaniline | 0.10 | 585 | — |
| 2-azido-6-methylaniline | 0.10 | 1,050 | — |
| 2-azido-4-methoxyaniline | 0.10 | >1,440 | — |

It is to be understood that the above disclosure is by way of specific example and that numerous modifications and variations are available to those of ordinary skill in the art without departing from the true spirit and scope of the invention.

We claim:

1. A gasoline motor fuel composition comprising a major amount of gasoline and a minor amount of an aryl o-aminoazide having the following general formula

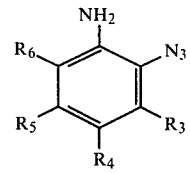

wherein each R group is independently selected from hydrogen, alkyl having from one to about four carbon atoms, alkenyl having from two to about four carbon atoms, haloalkyl having from one to about four carbon atoms, aryl having from six to about ten carbon atoms, cycloalkyl having from five to about eight carbon atoms, alkoxy having from one to about four carbon atoms, carbalkoxy having from two to about five carbon atoms, carbaryloxy having from seven to about nine carbon atoms, alkylamino having from one to about four carbon atoms, acyl having from two to about five carbon atoms, hydroxyl, amino, cyano, nitro, halo and halophenyl, or wherein any two adjacent R groups containing a total of four carbon atoms are joined together in a saturated or unsaturated ring.

2. A gasoline motor fuel composition in accordance with claim 1 wherein each R group is independently selected from hydrogen and at least one alkyl group having from one to about four carbon atoms.

3. A gasoline motor fuel composition in accordance with claim 1 wherein each R group is independently selected from hydrogen and at least one halo group.

4. A gasoline motor fuel composition in accordance with claim 1 wherein each R group is independently selected from hydrogen and at least one amino group.

5. A gasoline motor fuel composition in accordance with claim 1 wherein each R group is independently selected from hydrogen and at least one lower alkoxy group having from one to about four carbon atoms.

6. A gasoline motor fuel composition in accordance with claim 1 wherein said aryl o-aminoazide is o-azidoaniline.

7. A composition in accordance with claim 1 wherein said gasoline motor fuel contains from about 0.1 to about 50 grams of the said aryl o-aminoazide per gallon of gasoline.

8. A composition in accordance with claim 1 wherein said gasoline motor fuel contains from about 0.5 to about 15 grams of the said aryl o-aminoazide per gallon of gasoline.

9. A composition in accordance with claim 1 wherein said motor gasoline also contains a metallic antiknock agent.

10. A composition in accordance with claim 9 wherein the said metal antiknock agent is tetraethyl lead.

11. A composition in accordance with claim 9 wherein the said metal antiknock agent is manganese methylcyclopentadienyl tricarbonyl.

* * * * *